United States Patent
Moszner et al.

(10) Patent No.: US 10,213,367 B2
(45) Date of Patent: Feb. 26, 2019

(54) DENTAL MATERIALS WITH DEBONDING-ON-DEMAND PROPERTIES

(71) Applicants: Ivoclar Vivadent AG, Schaan (LI); Technische Universität Wien, Vienna (AT)

(72) Inventors: Norbert Moszner, Mauren (LI); Kai Rist, Feldkirch (AT); Iris Lamparth, Grabs (CH); Peter Burtscher, Rankweil (AT); Christian Gorsche, Vienna (AT); Robert Liska, Schleinbach (AT)

(73) Assignee: Ivoclar Vivadent AG, Schaan (LI)

( * ) Notice: Subject to any disclaimer, the term of this patent is extended or adjusted under 35 U.S.C. 154(b) by 0 days.

(21) Appl. No.: 15/325,142

(22) PCT Filed: Jul. 9, 2015

(86) PCT No.: PCT/EP2015/065779
§ 371 (c)(1),
(2) Date: Jan. 10, 2017

(87) PCT Pub. No.: WO2016/005540
PCT Pub. Date: Jan. 14, 2016

(65) Prior Publication Data
US 2017/0156993 A1 Jun. 8, 2017

(30) Foreign Application Priority Data
Jul. 11, 2014 (EP) .................. 14176730

(51) Int. Cl.
C08F 2/46 (2006.01)
C08F 2/50 (2006.01)
C08G 61/04 (2006.01)
A61K 6/083 (2006.01)
A61K 6/00 (2006.01)

(52) U.S. Cl.
CPC .......... *A61K 6/0835* (2013.01); *A61K 6/0023* (2013.01); *A61K 6/0052* (2013.01); *A61K 6/0088* (2013.01); *A61K 6/083* (2013.01)

(58) Field of Classification Search
CPC .. A61K 6/0835; A61K 6/0023; A61K 6/0052; A61K 6/0088
USPC ................ 522/66, 6, 71, 189, 184, 1; 520/1
See application file for complete search history.

(56) References Cited

U.S. PATENT DOCUMENTS

| 6,411,212 B1 | 6/2002 | Hecht et al. |
| 8,916,267 B2 | 12/2014 | Bauer et al. |
| 9,320,686 B2 | 4/2016 | Moszner et al. |
| 2007/0142494 A1 * | 6/2007 | Kalgutkar ............ A61K 6/0061 523/115 |
| 2007/0142497 A1 | 6/2007 | Kalgutkar et al. |
| 2007/0142498 A1 | 6/2007 | Brennan et al. |
| 2012/0016052 A1 * | 1/2012 | Bowman .................. C08F 2/38 522/168 |
| 2013/0090404 A1 * | 4/2013 | Bock .................... A61K 6/0023 522/28 |
| 2014/0329929 A1 * | 11/2014 | Moszner ............ A61K 6/0002 523/116 |

FOREIGN PATENT DOCUMENTS

| CA | 2674349 A1 | 1/2008 |
| EP | 2029630 A1 * | 3/2009 ............... A61K 6/09 |

OTHER PUBLICATIONS

Hammesfahr et al, EP 2029630 Machine Translation, Mar. 4, 2009 (Year: 2009).*
Gorsche et al, Exploring the benefits of b-allyl sulfones for more homogeneous dimethacrylate photopolymer networks, Jan. 5, 2015, polym. chem, 6, 2038-2047 (Year: 2015).*
Wojtecki, R. J. et al., "Using the dynamic bond to access macroscopically responsive structurally dynamic polymers," Nature Materials, 2011, 10, 14-27. McMillan Publishers Limited.
Quinn, S., "Chemical blowing agents: providing production, economic and physical improvements to a wide range of polymers," Plastics Additives & Compounding, May 2001.
Braun, D., Jakobi, R., "Synthesis and Decomposition of Azo-Initiators,I," Chemical Monthly, 113, 1403-1414, 1982.
International Preliminary Report on Patentability of PCT/EP2015/065779, dated Jan. 17, 2017, 12 pages.

* cited by examiner

*Primary Examiner* — Jessica Whiteley
(74) *Attorney, Agent, or Firm* — Ann M. Knab; Thad McMurray (57) ABSTRACT

Radically polymerizable dental material, which contains at least one compound of Formula I:

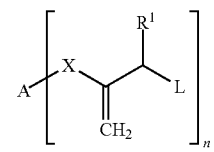

and at least one thermolabile radically polymerizable compound and/or at least one photolabile radically polymerizable compound. The materials are characterized by debonding-on-demand properties.

22 Claims, 3 Drawing Sheets

Progression of storage modulus of networks A1 (-.-), A2 (...),
A3 (===), A4 (---) and A5 (—)

Fig. 4

Loss factor of networks A1 (-.-), A2 (...), A3 (===),
A4 (---) und A5 (—).

DENTAL MATERIALS WITH DEBONDING-ON-DEMAND PROPERTIES

CROSS-REFERENCE TO RELATED APPLICATIONS

This application is a National Stage application of International patent application PCT/EP2015/065779 filed on Jul. 9, 2015, which claims priority to European patent application No. 14176730.1 filed on Jul. 11, 2014, the disclosures of which are incorporated herein by reference in their entirety.

FIELD OF THE INVENTION

The present invention relates to thermally curing and/or light-curing materials with debonding-on-demand (DoD) properties which are particularly suitable as dental adhesives or cements for example for securing inlays, onlays, crowns or bridges.

BACKGROUND

Dental composite cements contain a polymerizable organic matrix and one or more fillers, which are usually surface-modified with a polymerizable adhesion promoter. Depending on the type of fillers, the monomer matrix and the application, the fill level can vary between approx. 20 and 80 wt.-%

As a rule, the polymerizable organic matrix contains a mixture of monomers, initiator components, stabilizers and pigments. Mixtures of dimethacrylates are usually used as resins. Examples of this are the highly viscous dimethacrylates 2,2-bis[4-(2-hydroxy-3-methacryloyloxypropyl)phenyl]propane (bis-GMA) and 1,6-bis-[2-methacryloyloxy-ethoxycarbonylamino]-2,4,4-trimethylhexane (UDMA) or the dimethacrylates of lower viscosity used as diluting monomers, such as e.g. bismethacryloyloxymethyltricyclo[5.2.1.]decane (TCDMA), decanediol-1,10-dimethacrylate ($D_3MA$) and triethylene glycol dimethacrylate (TEGDMA).

In the radical polymerization of dental composite cements based on cross-linking dimethacrylates, a 3-dimensional polymer network already forms within a few seconds at the so-called gel point and thus a high mechanical strength develops, with the result that a simple, non-destructive debonding of the substrates or parts bonded using these cements, such as e.g. the bonding of a ceramic crown to a tooth stump, is possible only with difficulty or not at all. The early formation of a 3-dimensional network additionally results in a relatively high polymerization shrinkage stress (PCS) because the polymerization shrinkage can no longer be compensated for by a viscous flow of the monomers.

Adhesive bonds that can be debonded again are increasingly important in various technological fields. Examples are the detachment of components within the framework of automated manufacturing processes, the repair of complex components with adhesively bonded partial components or the simplification of the separation of materials when recycling such components at the end of the product's life. The debonding of adhesive bonds can be achieved on demand for example by significantly reducing the strength of the adhesive bond layer by heating.

Thus DE 198 32 629 A1 describes an adhesive system for forming reversible adhesive bonds based on polyurethanes, polyureas or epoxy resins, in which an additional component can be activated by introducing energy such that the adhesive components degrade. For example, organic bases or acids which degrade the adhesive resin can be released from blocked precursors by introducing heat or radiation energy.

WO 2010/128042 A1 describes industrial adhesive compositions for debondable adhesive bonds for aircraft or motor vehicle construction which consist of a customary adhesive matrix and a particulate expansion material such as e.g. azodicarbonamide. The components are debonded by heating the adhesive bond at least to the expansion temperature of the expansion material.

In dentistry, the debonding of adhesive bonds is important among other things in orthodontics, where brackets which are adhesively bonded to the tooth surface to correct malocclusions must be removed again without damaging the tooth enamel after successful correction. Moreover, in the case of repair or complete replacement of high-strength ceramic restorations or crowns which can be removed mechanically only laboriously, cement bonds that can be easily softened or separated would be advantageous.

In connection with orthodontic applications, US 2007/0142498 A1 describes dental compositions which contain thermally controllable additives such as e.g. thermoplastic polymers.

US 2007/0142497 A1 discloses dental compositions based on dimethacrylates with acid-labile tertiary carbonate groups and photoacids such as e.g. triarylsulfonium salts. These compositions can be photochemically cured using light in the visible range with suitable initiators such as, for instance, the bisacylphosphine oxide Irgacure 819 (photobonding) and softened again by irradiation with UV light at increased temperature (photothermal debonding).

WO 2013/034777 A2 and WO 2013/034778 A2 disclose dental materials which contain thermolabile or photolabile polymerizable compounds. The materials can be debonded again from the substrate by introducing heat or by irradiation with light in the UV or visible wavelength range.

SUMMARY

The object of the invention is to provide polymerizable dental materials, with debonding-on-demand properties, which display good substrate adhesion, in particular to tooth structure and/or dental ceramics, are characterized by a reduced polymerization shrinkage stress (PCS) and by an improved impact strength and above all are suitable as adhesives or composite cements.

BRIEF DESCRIPTION OF THE FIGURES

Other advantages, details and characteristics can be seen from the following description and drawings wherein.

DETAILED DESCRIPTION

The object is achieved according to the invention by compositions which contain at least one compound of Formula I, preferably in combination with a thermolabile radically polymerizable compound and/or a photolabile radically polymerizable compound:

The following meanings apply:

A H; —CN; a phenyl residue which can carry one or more substituents, such as $CH_3$, $C_2H_5$, OH, $OCH_3$, O—$COCH_3$, a polymerizable vinyl, (meth)acryloyloxy or (meth)acrylamide group; or an aliphatic linear or branched $C_1$-$C_{20}$ alkylene residue which can be interrupted by one or more 1,4-phenylene groups, urethane groups, O or S and which can carry in the terminal position a polymerizable vinyl, (meth)acryloyloxy or (meth)acrylamide group;

$R^1$ H, an aliphatic linear or branched $C_1$-$C_9$ alkyl residue, tolyl or phenyl;

L $SR^2$, CO-phenyl, $SO_2R^3$, $PO(R^4R^5)$, $PO(OR^6)(R^7)$, $PO(OR^8)(OR^9)$ or halogen, wherein $R^{2-9}$ in each case independently of each other are a phenyl residue which can carry one or more substituents, such as $CH_3$, $C_2H_5$, OH, $OCH_3$, —O—$COCH_3$, a polymerizable vinyl, (meth)acryloyloxy, (meth)acrylamide group, —C($=CH_2$)—$COOR^{11}$ or —C($=CH_2$)—CO—$NR^{12}R^{13}$; or are an aliphatic linear or branched $C_1$-$C_{20}$ alkylene residue which can be interrupted by O or S and which can carry in the terminal position a polymerizable vinyl, (meth)acryloyloxy, (meth)acrylamide group, —C($=CH_2$)—$COOR^{11}$ or —C($=CH_2$)—CO—$NR^{12}R^{13}$, wherein $R^{11-13}$ in each case independently of each other are a linear or branched $C_{1-6}$ residue;

X —COO—, —$CON(R^{10})$— or is absent, wherein the bond to A takes place via O or N and wherein $R^{10}$ is H; or an aliphatic linear or branched $C_1$-$C_{20}$ alkylene residue which can be interrupted by one or more O or S and which can carry in the terminal position a polymerizable vinyl, (meth)acryloyloxy, (meth)acrylamide group, —C($=CH_2$)—$COOR^{11}$ or —C($=CH_2$)—CO—$NR^{12}R^{13}$, wherein $R^{11-13}$ in each case independently of each other are a linear or branched $C_{1-6}$ residue;

n an integer from 1 to 6.

Preferred halogens are chlorine or bromine.

The formula extends only to those compounds which are compatible with the theory of chemical valence. For example, when A is hydrogen, n can only be 1. The indication that a radical is interrupted by one or more aromatics, urethane groups, O, S etc. is to be understood to mean that these groups are inserted into the carbon chain of the residue. These groups are thus bordered on both sides by C atoms and cannot be terminal. $C_1$ radicals cannot be interrupted.

The compounds of Formula I contain at least one radically polymerizable group, wherein compounds with 2 to 8 and in particular compounds with 2 to 4 radically polymerizable groups are preferred.

The variables preferably have the following meanings:

A H, —CN, a phenyl residue, an aliphatic linear or branched $C_1$-$C_{15}$ alkyl residue which can be interrupted by one or more 1,4-phenylene groups, urethane groups or O and which can carry in the terminal position a polymerizable (meth)acryloyloxy group;

$R^1$ H, phenyl, tolyl, an aliphatic linear $C_1$-$C_3$ alkyl residue;

L $SR^2$ or $SO_2R^3$, wherein $R^{2-3}$ in each case independently of each other are an aliphatic linear or branched $C_1$-$C_{20}$ alkylene residue which can be interrupted by O and which can carry in the terminal position a polymerizable (meth)acryloyloxy group or —C($=CH_2$)—$COOR^{11}$, wherein $R^{11}$ is a linear or branched $C_{1-3}$ residue; or a phenyl residue which can carry one or more substituents, preferably $CH_3$, $C_2H_5$, $OCH_3$ and/or O—$COCH_3$;

X —COO— or —$CON(R^{10})$—, wherein $R^{10}$ is methyl, or is absent;

n 1 or 2.

Particularly preferred are compounds of Formula I in which at least one and preferably all of the variables have the following meaning:

A a saturated, linear aliphatic hydrocarbon residue with 1 to 12 carbon atoms which can be interrupted by one or more 1,4-phenylene groups, urethane groups or O and which can carry a methacryloyloxy group, X —COO— or —$CON(R^{10})$—, wherein $R^{10}$ is methyl, or is absent;

$R^1$ H,

L —$SO_2R^3$, wherein $R^3$ is $CH_3$ or tolyl, n 1 or 2.

Quite particularly preferred are compounds of Formula I in which the variables have the following meanings:

A a saturated, linear aliphatic hydrocarbon residue with 6 to 12 carbon atoms which can be interrupted by 1 to 3 O atoms,

X —COO—;

$R^1$ H,

L $SO_2R^3$, wherein $R^3$ is $CH_3$ or tolyl, n 1 or 2.

Some polymerization-transfer-active compounds of Formula I are known and can be easily prepared using known synthesis methods. Thus the iodine compounds I-L can be added to an unsaturated derivative as shown below and subsequently the compounds of Formula I according to the invention are obtained by HI cleavage:

A specific example is:

Preferred examples of the polymerization-transfer-active compounds of Formula I according to the invention are:

-continued

The compounds of Formula I make it possible to control or regulate the network structure during radical polymerization. They lead to a significantly delayed gel formation and thus to a longer gel time, meaning that the 3-dimensional polymer network forms later. A lower PCS is therefore achieved during the curing of the resins or corresponding composites, which is a great advantage for a dental application e.g. as filling material. Furthermore, the polymerization-transfer-active compounds of Formula I surprisingly also yield more homogeneous polymer networks with a narrower glass transition, meaning that the glass transition takes place in a narrower temperature range. This has the advantage that chain tensions can be better degraded by relaxation processes and a quicker debonding-on-demand (DoD) can be effected. It is particularly advantageous that the glass transition temperature is significantly reduced. As a result of the reduced glass transition temperature, the polymers can be softened at lower temperatures. This permits, e.g. in the case of adhesives and cements, an on-demand debonding of the adhesive bond (debonding-on-demand) even under oral conditions. The reduced glass transition temperature has the further advantage that polymer materials with improved impact strength are obtained.

In order to improve the debonding-on-demand effect, the compositions according to the invention preferably contain, in addition to the compounds of Formula I, at least one thermolabile radically polymerizable compound and/or at least one photolabile radically polymerizable compound.

By thermolabile and photolabile compounds are meant those monomers which contain groups which can be cleaved thermally or by irradiation respectively. In contrast, with compounds of Formula I, polymers can be obtained which, although they can be softened by an increase in temperature, do not themselves cleave. If thermolabile monomers are combined with compounds of Formula I, polymers result which soften at relatively low temperatures and additionally can be thermally cleaved. If compounds of the formula are combined with photolabile monomers, polymers are produced which soften at relatively low temperatures and additionally can be photochemically cleaved. Finally, compounds of Formula I can be combined with mixtures of a thermolabile monomer and a photolabile monomer, whereby polymers can be obtained which exhibit a combination of these features. It was found according to the invention that a combination of compounds of Formula I with thermo- and/or photolabile monomers has an advantageous effect on the debonding-on-demand properties of the cured materials.

Particularly suitable thermolabile and photolabile radically polymerizable compounds are thermolabile multifunctional (meth)acrylates and photolabile multifunctional (meth)acrylates, in particular thermolabile di(meth)acrylates and photolabile di(meth)acrylates, i.e. di(meth)acrylates with at least one thermolabile or photolabile group. Materials which contain thermolabile co-monomers are preferred. By polyfunctional (meth)acrylates are meant compounds with two or more, preferably 2 to 4, radically polymerizable groups. Di(meth)acrylates correspondingly contain 2 (meth) acrylate groups.

Further preferred are thermolabile multifunctional (meth)acrylamides and photolabile multifunctional (meth)acrylamides, in particular thermolabile di(meth)acrylamides and photolabile di(meth)acrylamides.

Suitable thermolabile groups are known per se. These are characterized in that they contain one or more thermolabile covalent bonds. Preferred thermolabile groups with thermolabile covalent bonds include thermolabile cycloaddition adducts such as Diels-Alder adducts, hetero-Diels-Alder adducts as well as thermolabile alkoxyamine, oxime ester, oxime urethane or azo groups. Examples of thermolabile groups are also described in R. J. Wojtecki et al., *Nature Materials* 2011, 10, 14-27.

Particularly preferred are those compounds in which the thermolabile group is bonded to two polymerizable (meth) acrylamide groups and in particular (meth)acrylate groups.

Preferred examples of thermolabile cross-linking monomers are polyfunctional (meth)acrylates or (meth)acrylamides with at least one thermolabile group between two (meth)acryl or (meth)acrylamide groups. Preferred thermolabile compounds are Diels-Alder adducts such as the Diels-Alder adduct from furfuryl methacrylate and N-(3-(methacryloyloxy)propyl)-maleimide, the reaction products of N-hydroxy-(meth)acrylamide with di- or triisocyanates such as hexamethylene-1,6-diisocyanate (HDI), 2,2,4-trimethyl-hexamethylene-1,6-diisocyanate or the HDI trimer, as well as products which are obtained by the stoichiometric reaction of di- or triisocyanates with 1-hydroxymethylacrylic acid esters such as 1-hydroxymethylacrylic acid ethyl ester or with β-keto ester (meth)acrylates such as 2-acetoacetoxy-ethyl methacrylate.

Thermolabile cross-linking monomers which release gas are also very suitable. Examples are the esterification products of azobis(4-cyanovaleric acid) with hydroxyalkyl (meth)acrylates such as hydroxyethyl (meth)acrylate or hydroxypropyl (meth)acrylate or with N-(hydroxyalkyl) (meth)acrylamides such as N-(5-hydroxypentyl)methacrylamide or N-methyl-N-(2-hydroxyethyl) acrylamide.

Suitable photolabile groups are also known per se. These are characterized in that they contain one or more photolabile covalent bonds. Preferred photolabile groups with photolabile covalent bonds include benzoin ethers, oxyalkyl-phenylacetophenones, dialkyloxyacetophenones, benzoyl diphenylphosphine oxides, dibenzoyl phenylphosphine oxides, dialkyl benzoyl and dialkyl dibenzoyl germanium derivatives. In particular, those compounds are preferred which contain one photolabile group and two polymerizable (meth)acrylate groups. Preferred compounds are bis-(4-methacryloyloxybenzoyldiethyl germanium, bis-{4-[2-(methacryloyloxy)diethylcarbamoyloxybenzoyl}diethyl germanium, bis-[3-(methacryloyloxymethyl)-2,4,6-trimethylbenzoyl]phenylphosphine oxide and methacrylic acid 2-[2-(4-{2-methyl-2-[2-(methacryloyloxy)ethylcarbamoyloxy]-propionyl}-phenoxy)-ethoxycarbonylamino]ethyl ester.

Moreover the thermolabile or photolabile monomers described in WO 2013/034777 A2 and WO 2013/034778 A2 are very suitable.

The dental materials according to the invention preferably also contain, optionally in addition to the thermolabile or photolabile polymerizable compounds, one or more further radically polymerizable monomers, particularly preferably at least one multifunctional (meth)acrylate or a mixture of mono- and multifunctional (meth)acrylates. Here too, by monofunctional (meth)acrylates are meant compounds with one, by polyfunctional (meth)acrylates compounds with two or more, preferably 2 to 4, radically polymerizable groups. According to a quite particularly preferred embodiment, the compositions according to the invention contain at least one dimethacrylate or a mixture of mono- and dimethacrylates.

Examples of particularly suitable mono- or multifunctional (meth)acrylates are methyl, ethyl, 2-hydroxyethyl, butyl, benzyl, tetrahydrofurfuryl or isobornyl (meth)acrylate, p-cumyl phenoxyethylene glycol methacrylate (CMP-1E), bisphenol A di(meth)acrylate, bis-G(M)A (an addition product of (meth)acrylic acid and bisphenol-A-diglycidyl ether), ethoxylated or propoxylated bisphenol-A-di(meth) acrylate, such as e.g. the bisphenol-A-dimethacrylate SR-348c (Sartomer) with 3 ethoxygroups or 2,2-bis[4-(2-(meth)acryloxypropoxy)phenyl]-propane, UD(M)A (an addition product of 2-hydroxyethyl (meth)acrylate and 2,2, 4-trimethyl hexamethylene diisocyanate), di-, tri- or tetra-ethylene glycol di(meth)acrylate, trimethylolpropane tri (meth)acrylate, pentaerythritol tetra(meth)acrylate, as well as glycerol di- and tri(meth)acrylate, 1,4-butanediol di(meth)acrylate, 1,10-decanediol di(meth)acrylate (D₃MA) or 1,12-dodecanediol di(meth)acrylate.

In addition to the above-named co-monomers, the dental materials according to the invention can preferably also contain radically polymerizable, acid-group-containing monomers (adhesive monomers). Preferred acid groups are carboxylic acid groups, phosphonic acid groups, phosphoric acid groups and sulfonic acid groups. Preferred monomers with carboxylic acid groups are maleic acid, acrylic acid, methacrylic acid, 2-(hydroxymethyl) acrylic acid, 4-(meth) acryloyloxyethyltrimellitic acid anhydride, 10-methacryloyloxydecylmalonic acid, N-(2-hydroxy-3-methacryloyloxy propyl)-N-phenylglycine and 4-vinylbenzoic acid. Preferred monomers with phosphonic acid groups are vinylphosphonic acid, 4-vinylphenylphosphonic acid, 4-vinylbenzylphosphonic acid, 2-methacryloyloxyethylphosphonic acid, 2-methacrylamidoethylphosphonic acid, 4-methacrylamido-4-methyl-pentylphosphonic acid, 2-[4-(dihydroxyphosphoryl)-2-oxa-butyl]-acrylic acid, 2-[4-(dihydroxyphosphoryl)-2-oxa-butyl]-acrylic acid ethyl and -2,4,6-trimethylphenyl ester. Preferred monomers with phosphoric acid groups are 2-methacryloyloxypropyl mono- or dihydrogen phosphate, 2-methacryloyloxyethyl mono- or dihydrogen phosphate, 2-methacryloyloxyethylphenyl hydrogen phosphate, dipentaerythritolpentamethacryloyloxyphosphate, 10-methacryloyl-oxydecyl dihydrogen phosphate, phosphoric acid mono-(1-acryloyl-piperidin-4-yl)ester, 6-(methacrylamidohexyl dihydrogen phosphate and 1,3-bis-(N-acryloyl-N-propylamino)-propan-2-yl dihydrogen phosphate. Preferred monomers with sulfonic acid groups are vinylsulfonic acid, 4-vinylphenylsulfonic acid and 3-(methacrylamido)propyl sulfonic acid.

To initiate the radical polymerization, the compositions according to the invention preferably contain an initiator for the radical polymerization, particularly preferably a photoinitiator. Suitable in particular as photoinitiators are benzophenone, benzoin and derivatives thereof or α-diketones or derivatives thereof, such as 9,10-phenanthrenequinone, 1-phenyl-propane-1,2-dione, diacetyl or 4,4'-dichlorobenzil. Camphorquinone (CQ) and 2,2-dimethoxy-2-phenyl-acetophenone are preferably used, and particularly preferably α-diketones combined with amines as reducing agents, such as e.g. 4-(dimethylamino)-benzoic acid ester (EDMAB), N,N-dimethylaminoethyl methacrylate, N,N-dimethylsym.-xylidine or triethanolamine. Norrish type I photoinitiators, above all acyl or bisacylphosphine oxides are also suitable, and monoacyltrialkyl or diacyldialkyl germanium compounds, such as e.g. benzoyltrimethylgermanium, dibenzoyldiethylgermanium or bis(4-methoxybenzoyl)diethylgermanium (MBDEGe) are particularly suitable. Mixtures of the different photoinitiators can also be used, such as e.g. bis(4-methoxybenzoyl)diethylgermanium combined with camphorquinone and 4-dimethylaminobenzoic acid ethyl ester.

According to a preferred embodiment, the dental materials according to the invention additionally contain organic or inorganic particulate filler, particularly preferably one or more inorganic particulate fillers.

Particularly suitable are fillers based on oxides with a particle size of from 0.01 to 15 μm, such as $SiO_2$, $ZrO_2$ and $TiO_2$ or mixed oxides of $SiO_2$, $ZrO_2$, $ZnO$ and/or $TiO_2$, nanoparticulate or microfine fillers with a particle size of from 10 to 300 nm, such as pyrogenic silica or precipitated silica as well as glass powders with a particle size of from 0.01 to 15 μm, preferably from 0.2 to 1.5 μm, such as quartz, glass ceramic or X-ray opaque glass powders of e.g. barium or strontium aluminium silicate glasses, and X-ray opaque fillers with a particle size of from 0.2 to 5 μm, such as ytterbium trifluoride, tantalum(V) oxide, barium sulfate or mixed oxides of $SiO_2$ with ytterbium(III) oxide or tantalum (V) oxide. Fibrous fillers, nanofibres or whiskers are also not excluded. Unless otherwise indicated, all particle sizes are weight-average particle sizes.

Fillers are divided, according to particle size, into macrofillers and microfillers. Macrofillers are obtained by grinding quartz, X-ray opaque glasses, borosilicates or ceramic, are of a purely inorganic nature and mostly consist of splinter-like particles. Macrofillers with an average particle size of from 0.2 to 10 μm are preferred. Pyrogenic $SiO_2$ or precipitated silica are preferably used as microfillers, or also mixed oxides, e.g. $SiO_2$—$ZrO_2$, which are available by hydrolytic co-condensation of metal alkoxides. The microfillers preferably have an average particle size of from approx. 5 to 100 nm.

The preferred filler content conforms to the desired application. Adhesives preferably contain 0 to 20 wt.-% and cements and composites preferably 20 to 80 wt.-% filler, in each case relative to the total mass of the material.

To improve the bond between the filler particles and the cross-linked polymerization matrix, $SiO_2$-based fillers can be surface-modified with (meth)acrylate-functionalized silanes. A preferred example of such silanes is 3-(meth) acryloyloxypropyltrimethoxysilane. To surface-modify non-silicate fillers, such as e.g. $ZrO_2$ or $TiO_2$, functionalized acid phosphates, such as e.g. 10-(meth)acryloyloxydecyl dihydrogen phosphate can also be used.

The dental materials according to the invention can additionally contain a thermally gas-releasing additive. Preferred gas-releasing additives are e.g. azo compounds such as azodicarbonamide, 2,2'-azobisisobutyronitrile or 2,2'-azobis (4-cyanopentanoic acid), N-nitroso compounds, hydrazides such as benzenesulfonyl hydrazide, peroxides such as dicumol peroxide or acetonedicarboxylic acid. Examples of such compounds are described, for instance, in St. Quinn, *Plastics, Additives & Compounding* 2001, 3, 16-21. The decomposition temperature, for example in the case of azo compounds, can be set in a manner known per se by the substituent pattern (cf. D. Braun, R. Jakobi, *Monatshefte Chemie* 1982, 113, 1403-1414).

Furthermore, the dental materials according to the invention can contain an additive which can convert radiated electromagnetic radiation into heat. Such so-called radiation-to-heat converters are organic, inorganic or organometallic substances or hybrid components which are capable of converting UV, NIR or IR radiation, visible light, microwave or radiowave radiation into heat in order to cleave thermolabile groups. Examples of this are dyes and pigments that absorb UV, NIR or IR radiation. Examples of dyes that absorb in the IR range are azo, methine, anthraquinone or porphyrin dyes. Examples of pigments that absorb NIR radiation are antimony and indium tin oxide, phthalocyanine pigments, soot, Ni and Pt dithiolene complexes. Examples of compounds that absorb in the UV range are benzotriazoles, triazines, benzophenones, cyanoacrylates, salicylic acid derivatives and hindered amine light stabilizers (HALS). Examples of additives that absorb in the frequency range of microwaves (1 to 300 GHz) or radiowaves (10 kHz to 1 GHz) are ferromagnetic ceramic substances, so-called ferrites which are composed of the iron oxides haematite ($Fe_2O_3$) or magnetite ($Fe_3O_4$) and further oxides for example of the metals Zn, Mn, or Ni and are commercially available as powders.

Optionally, the compositions used according to the invention can contain one or more further additives, above all solvents such as water, ethanol or corresponding solvent mixtures, stabilizers, dyes, fluoride-ion-releasing additives, optical brighteners, plasticizers or UV absorbers.

The preferred solvent content conforms to the desired application. Adhesives preferably contain 0 to 60 wt.-% and particularly preferably 1 to 50 wt.-% solvent. In contrast, cements preferably contain no solvent.

The debonding properties of the dental materials according to the invention can be influenced in a targeted manner by the composition of the materials and adapted to the desired intended application. Thus, the ability to debond on demand by heating or irradiation increases with the concentration of thermolabile or photolabile components used, i.e. in particular of the thermolabile or photolabile cross-linking monomers and gas-releasing additives. Furthermore, the debonding properties can also be varied by the selection of the co-monomers, wherein the cross-linking density and thus also the strength and the elastic modulus can be varied with the proportion of cross-linking monomers or by addition of monofunctional monomers.

The dental materials according to the invention preferably contain 0.5 to 60 wt.-%, preferably 1.0 to 50 wt.-% and particularly preferably 1.0 to 40 wt.-% of at least one compound of general formula I.

In addition, the materials preferably also contain 0.01 to 5.0 wt.-%, preferably 0.1 to 5.0 wt.-% and particularly preferably 0.1 to 3.0 wt.-% initiator(s) for the radical polymerization, particularly preferably a photoinitiator, and particularly preferably also 1 to 60 wt.-%, preferably 5 to 50 wt.-% and particularly preferably 5 to 40 wt.-% difunctional thermo- and/or photolabile (meth)acrylate(s).

Furthermore, the dental materials according to the invention preferably contain 0 to 80 wt.-%, preferably 0 to 70 wt.-% and particularly preferably 0 to 60 wt.-% filler(s), wherein the filler content is matched to the planned use of the materials, as described above.

Moreover, the dental materials according to the invention preferably contain 0 to 40 wt.-%, preferably 0 to 30 wt.-% and particularly preferably 5 to 30 wt.-% expanding additive(s) and/or radiation-to-heat converters, and optionally 0 to 5 wt.-%, preferably 0 to 3 wt.-%, particularly preferably 0.5 to 3 wt.-% other additive(s).

According to the invention, dental materials which contain the following components are particularly preferred:
(a) 1 to 80 wt.-%, preferably 10 to 70 wt.-% and particularly preferably 10 to 60 wt.-% multifunctional (meth)acrylate(s),
(b) 0.01 to 5.0 wt.-%, preferably 0.1 to 5.0 wt.-% and particularly preferably 0.1 to 3.0 wt.-% initiator(s),
(c) 0.5 to 60 wt.-%, preferably 1.0 to 50 wt.-% and particularly preferably 1.0 to 40 wt.-% of at least one compound of general formula I,
(d) 0 to 50 wt.-%, preferably 0 to 40 wt.-% and particularly preferably 0 to 30 wt.-% monofunctional (meth)acrylate(s),
(e) 1 to 60 wt.-%, preferably 5 to 50 wt.-% and particularly preferably 5 to 40 wt.-% difunctional thermo- and/or photolabile (meth)acrylate(s),
(f) 0 to 80 wt.-%, preferably 0 to 70 wt.-% and particularly preferably 0 to 60 wt.-% filler(s),
(g) 0 to 40 wt.-%, preferably 0 to 30 wt.-% and particularly preferably 5 to 30 wt.-% expanding additive(s) and/or radiation-to-heat converters,
(h) 0 to 60 wt.-%, preferably 0 to 50 wt.-%, particularly preferably 1 to 50 wt.-% solvent(s) and
(i) 0 to 5 wt.-%, preferably 0 to 3 wt.-%, particularly preferably 0.5 to 3 wt.-% other additive(s).

Unless otherwise stated, all quantities relate to the total mass of the composition. The individual quantity ranges can be chosen separately.

Those dental materials that consist of the named components are quite particularly preferred. Furthermore, those materials are preferred in which the individual components are in each case selected from the above-named preferred and particularly preferred substances. Particularly preferred are materials which, in addition to the compound of Formula (I), do not contain volatile mercaptans, i.e. mercaptans which have a typical mercaptan odour. Quite particularly preferred are compositions which do not contain further mercaptans and preferably also do not contain other disulfides or thioethers.

The materials according to the invention are particularly suitable as dental adhesives and cements. They have similar mechanical properties (bending strength and elastic modulus) to materials based on dimethacrylates, but are characterized by a reduced polymerization shrinkage stress (PCS), debonding-on-demand properties, a narrow glass transition range, improved impact strength and low intrinsic odour.

The dental materials are suitable primarily for intraoral application by the dentist to restore damaged teeth (clinical materials). However, they can also be used extraorally, for example in the manufacture or repair of dental restorations (technical materials).

A subject of the invention is also the use of compounds of Formula I for the preparation of an adhesive or cement with debonding-on-demand properties.

The invention is explained in more detail below by means of embodiment examples.

EXAMPLES

Example 1

Synthesis of 2-(toluene-4-sulfonylmethyl)-acrylic Acid Lauryl Ester (1)

First of all, in a yellow-light laboratory, 3.81 g (15 mmol) iodine was dissolved in 70 ml ethanol and slowly added dropwise to a 0.1 M solution of sodium p-toluene sulfinate (15 mmol) in water. The yellow solid that forms, (4-methylbenzene-1-sulfonyl iodide, MBSI), was filtered and subsequently washed with water. The solid was then dissolved in $CH_2Cl_2$ (50 ml) and dried with anhydrous $Na_2SO_4$. The desiccant was filtered and the solution with the freshly prepared MBSI was stirred together with 2.54 g (10 mmol) lauryl methacrylate (LMA). The reaction was monitored using thin-layer chromatography (PE/EE 20/1). After all of the LMA had been used up, the reaction solution was washed with 5 wt.-% sodium dithionite solution (2×25 ml) and with water (1×25 ml). The aqueous phase was re-extracted with $CH_2Cl_2$ (1×25 ml) and the combined organic phases were dried over anhydrous $Na_2SO_4$. 50 ml ethyl acetate was then added to the solution and the $CH_2Cl_2$ was evaporated on a rotary evaporator. 5.06 g (50 mmol) triethylamine was then added to the reaction solution under an Ar atmosphere and then boiled under reflux overnight. Once the reaction was complete, the solution was washed with 1N HCl (2×50 ml) and dist. water (1×50 ml). The aqueous phases were re-extracted and the combined organic phases were dried over anhydrous $Na_2SO_4$. The solvent was drawn off on a rotary evaporator and the crude product was purified using column chromatography with a mixture of PE/EE 5/1 ($R_f$=0.39). The yield was approx. 28.8 g (73% theoretical).

$^1$H-NMR (200 MHz, $CDCl_3$, δ): 7.71 (d, J=8.2 Hz, 2H; Ar—H), 7.30 (d, J=8.2 Hz, 2H; Ar—H), 6.47 (s, 1H; =$CH_2$), 5.89 (s, 1H; =$CH_2$), 4.12 (s, 2H; —$SO_2$—$CH_2$—), 3.94 (t, 2H; —O—$\underline{CH_2}$—$CH_2$—), 2.42 (s, 3H; Ar—$CH_3$), 1.52 (m, 2H; —O—$CH_2$—$\underline{CH_2}$—), 1.25 (s, 18H; —O—$CH_2$—$CH_2$—$\underline{CH_2}$—$\underline{CH_2}$—$\underline{CH_2}$—$\underline{CH_2}$—$\underline{CH_2}$—$\underline{CH_2}$—$\underline{CH_2}$—$\underline{CH_2}$—$CH_3$); 0.86 (m, 3H; —$CH_2$—$\underline{CH_3}$);

$^{13}$C-NMR (50 MHz, $CDCl_3$, δ): 164.9 (C=O), 144.8 (C4), 135.5 (C4), 133.1 (C2), 129.6 (C3), 129.2 (C4), 128.8 (C3), 65.6 (C2), 57.5 (C2), 31.9 (C2), 29.6 (C2, C2, C2), 29.5 (C2), 29.3 (C2), 29.2 (C2), 28.4 (C2), 25.8 (C2), 22.7 (C2), 21.6 (C1), 14.1 (C1).

Example 2

Synthesis of Tetraethylene Glycol bis[2-(toluene-4-sulfonyl-methyl) Acrylate] (2)

Tetraethylene glycol dimethacrylate (TTEGDMA: 5.29 g, 16 mmol) and 4-toluenesulfonyl iodide (9.03 g, 32 mmol) were stirred together in $CH_2Cl_2$ (approx. 50 ml) at room temperature in yellow light. The reaction was monitored using $^1$H-NMR spectroscopy. After all of the TTEGDMA had been used up (decrease in the double-bond signals), the reaction solution was washed with 5 wt.-% sodium dithionite solution (2×25 ml) and with water (1×25 ml). The aqueous phase was re-extracted with $CH_2Cl_2$ (1×25 ml) and the combined organic phases were dried over $Na_2SO_4$. 50 ml ethyl acetate was then added to the solution and the $CH_2Cl_2$ was evaporated on a rotary evaporator. A further 50 ml ethyl acetate was then added to the reaction solution and triethylamine (8.1 g, 80 mmol) was added dropwise under an Ar atmosphere (solid precipitated out). The reaction solution was then boiled under reflux overnight. Once the reaction was complete, the solution was washed with 1N HCl (2×50 ml) and dist. water (1×50 ml). The aqueous phases were re-extracted and the combined organic phases were dried over $Na_2SO_4$. The solvent was drawn off on a rotary evaporator and the crude product was purified using column chromatography with a mixture of PE/EE 1/4. ($R_f$=0.32). Yield 70%.

$^1$H-NMR (200 MHz, $CDCl_3$, δ): 7.73 (d, J=8.2 Hz, 4H; Ar—H), 7.32 (d, J=8.2 Hz, 4H; Ar—H), 6.52 (s, 2H; =$CH_2$), 5.89 (s, 2H; =$CH_2$), 4.14 (m, 8H; OOC—$CH_2$—, $SO_2$—$CH_2$—), 3.62 (m, 12H; —$CH_2$—O—$CH_2$—$CH_2$—), 2.43 (s, 6H; Ar—$CH_3$).

$^{13}$C-NMR (50 MHz, $CDCl_3$, δ): 164.9 (C=O), 144.9 (C4), 135.4 (C4), 133.6 (C2), 129.7 (C3), 128.9 (C4), 128.8 (C4), 70.7 (C2), 68.8 (C2), 64.5 (C2), 57.5 (C2), 21.6 (C1).

Example 3

Synthesis of Triethylene Glycol bis[2-(toluene-4-sulfonylmethyl) Acrylate] (3)

In a brown glass flask, sodium p-toluenesulfinate (39.20 g, 0.22 mol) was reacted with iodine (55.83 g, 0.22 mol) and worked up according to Example 1 to prepare MBSI 1. The yellow solid was dissolved in dichloromethane (300 ml). Triethylene glycol dimethacrylate (28.63 g, 0.10 mol) was added and the reaction mixture was stirred at RT. After 24 h triethylamine (22.26 g, 0.22 mol) was added dropwise. The red-brown solution was stirred for 2 h at ambient temperature and then concentrated on a rotary evaporator. The dark brown oil was taken up in n-hexane/ethyl acetate 1:1 (100 ml) and filtered over a frit filled with silica gel (silica gel 60, n-hexane/ethyl acetate 1:1). The filtrate was concentrated on a rotary evaporator. The residue was dissolved in ethyl acetate (400 ml) and triethylamine (22.26 g, 0.22 mol) was added. The brownish solution was heated under reflux for 6 h. After cooling, the reaction solution was washed with hydrochloric acid (1N; 2×200 ml) and water (200 ml), dried over $Na_2SO_4$, filtered and concentrated on a rotary evaporator. The brownish oil was purified using column chromatography (silica gel 60, n-hexane/ethyl acetate 1:2; $R_f$=0.35). 48.44 g (81% yield) of a yellow oil was obtained.

$^1$H-NMR (200 MHz, $CDCl_3$, δ): 7.73 (d, J=8.2 Hz, 4H; Ar—H), 7.32 (d, J=8.2 Hz, 4H; Ar—H), 6.52 (s, 2H; =$CH_2$), 5.89 (s, 2H; =$CH_2$), 4.14 (m, 8H; OOC—$CH_2$—, $SO_2$—$CH_2$—), 3.62 (m, 12H; —$CH_2$—O—$CH_2$—$CH_2$—), 2.43 (s, 6H; Ar—$CH_3$);

$^{13}$C-NMR (50 MHz, $CDCl_3$, δ): 164.9 (C=O), 144.9 (C4), 135.4 (C4), 133.6 (C2), 129.7 (C3), 128.9 (C4), 128.8 (C4), 70.7 (C2), 68.8 (C2), 64.5 (C2), 57.5 (C2), 21.6 (C1);

Example 4

Synthesis of 2-propenoic Acid 2-[(diethoxyphosphinyl)-methyl]-ethyl Ester (4)

For the synthesis of 4, ethyl 2-bromomethylacrylate (1.5 g, 0.008 mol) was heated under reflux with distilled triethyl phosphite (1.3 g, 0.008 mol) for 7 h under an Ar atmosphere in a 10-ml round-bottomed flask and then reacted for 12 h at RT. The product was transferred into a pear-shaped flask and EtBr (bp=38° C. at 1.013 bar) was removed at 5 mbar. Purification using MPLC with petroleum ether (PE)/ethyl acetate (EE) 3:2 was then carried out ($R_f$~0.13). The yield of 4 purified using column chromatography was 1.6 g (82% theoretical).

$^1$H-NMR (200 MHz, $CDCl_3$, δ): 0.92-1.34 (9.1H, m, 3× —$CH_2$—$CH_3$), 2.77 (1H, d, J=0.78 Hz, =C(COOEt)-$CH_2$—PO(OEt)$_2$), 2.87 (1H, d, J=0.78 Hz, =C(COOEt)-$CH_2$—PO(OEt)$_2$), 3.87-4.18 (6.1H, m, 3× —O—$CH_2$—$CH_3$), 5.73 (1H, dd, J=5.46 Hz, J=0.78 Hz, $H_2$C=C(COOEt)-), 6.22 (1H, dd, J=5.66 Hz, J=0.58 Hz, $H_2$C=C(COOEt)—).

Example 5

Synthesis of 2-propenoic Acid 2-[(dodecylthio)methyl]-ethyl Ester (5)

For the synthesis of 5, triethylamine (1.1 g, 0.011 mol) and freshly distilled dodecylthiol (1.6 g, 0.008 mol) were placed in a 50-ml round-necked flask with 10 ml THF and ethyl 2-bromomethylacrylate (1.5 g, 0.008 mol) was flushed into the reaction flask with 9 ml THF. On addition of the acrylate a fine, white precipitate precipitated out immediately. The end of the reaction, after stirring at room temperature (RT) for 21 h, was confirmed using thin-layer chromatography (TLC). The working up was carried out by dissolving unreacted salt in 15 ml deionized water. The aqueous phase was extracted 3× with 15 ml petroleum ether, the combined organic phases were dried over $Na_2SO_4$ and PE was drawn off on a rotary evaporator. Purification using medium-pressure liquid chromatography (MPLC) with PE/EE 10:1 was then carried out ($R_f$~0.46 (PE/EE 12:1)). The yield of 5 purified using column chromatography was 1.2 g (50% theoretical).

$^1$H-NMR (200 MHz, $CDCl_3$, δ): 0.85 (3.5H, t, J=6.46 Hz, —$C_{10}H_{20}$—$CH_3$), 1.10-1.65 (27.1H, m, —$CH_2$—$C_{10}\underline{H}_{20}$—$CH_3$ and —O—$CH_2$—$C\underline{H}_3$), 2.42 (2.1H, t, J=7.24 Hz, —S—$C\underline{H}_2$—$C_{11}H_{23}$), 3.35 (2H, s, =C(COO$C_2H_5$)—$C\underline{H}_2$—S—), 4.21 (2.2H, q, J=7.11 Hz, —O—$C\underline{H}_2$—$CH_3$), 5.61 (1H, d, J=1.17 Hz, $\underline{H}_2$C=C(COO$C_2H_5$)—), 6.17 (1H, d, J=1.98 Hz, $\underline{H}_2$C=C(COO$C_2H_5$)—).

Example 6

Synthesis of 2-{[2-(ethoxycarbonyl)-2-propenyl]-sulfanyl]-methyl}-acrylic Acid Ethyl Ester (6)

For the synthesis of 6, ethyl 2-bromomethylacrylate (10.0 g, 0.052 mol) was placed in a 50-ml round-bottomed flask and sodium sulfide (5.9 g, 0.021 mol), freshly recrystallized from deionized $H_2O$, in 2 ml deionized $H_2O$ was added in one go and rinsed using 8 ml $H_2O$. Stirring was carried out for 24 h at RT and, after controlling the reaction using TLC, dilution was carried out with 15 ml deionized $H_2O$ to dissolve any salt formed. Extraction was carried out 3× with 15 ml petroleum ether, the combined organic phases were extracted with saturated saline solution and then dried over $Na_2SO_4$. After drawing off the solvent on a rotary evaporator, purification was carried out using MPLC in PE/EE 6:1 ($R_f$~0.49) and yielded 4.0 g 6 (30% theoretical yield).

$^1$H-NMR (200 MHz, $CDCl_3$, δ): 1.18 (6.1H, t, J=7.13 Hz, 2× —$CH_2$—$CH_3$), 3.20 (3.8H, d, J=0.58 Hz, 2× =C($COOC_2H_5$)—$CH_2$—S—), 4.10 (4.1H, q, J=7.11 Hz, —O—$CH_2$—$CH_3$), 5.55 (2H, d, J=0.98 Hz, 2× $H_2$C=C($COOC_2H_5$)—), 6.09 (2H, d, J=0.98 Hz, 2× $H_2$C=C($COOC_2H_5$)—).

Example 7

Synthesis of 2-{[2-(ethoxycarbonyl)-2-propenyl]-sulfonyl]-methyl}-acrylic Acid Ethyl Ester (7)

For the synthesis of 7, compound 6 (3.0 g, 0.012 mol) in 100 ml DMF was placed in a 500-ml round-necked flask, potassium peroxosulfate (13.9 g, 0.045 mol) was added and rinsed with 200 ml DMF. Stirring was carried out for 4 h at RT under an Ar atmosphere and, after controlling the reaction using TLC, deionized $H_2O$ (900 ml) was added. Extraction was carried out 3× with 130 ml diethyl ether, 1× with 150 ml saturated saline solution, followed by drying over $Na_2SO_4$. After drawing off the solvent on a rotary evaporator, purification was carried out using MPLC in PE/EE 10:1 ($R_f$~0.67 (PE/EE 1:1)) and yielded 1.2 g 7 (37% theoretical yield).

$^1$H-NMR (200 MHz, $CDCl_3$, δ): 1.24 (6.4H, t, J=7.14 Hz, 2× —$CH_2$—$CH_3$), 4.03 (4.1H, s, 2× =C($COOC_2H_5$)—C$H_2$—S—), 4.18 (4.1H, q, J=7.17 Hz, —O—$CH_2$—$CH_3$), 6.08 (2H, s, 2× $H_2$C=C($COOC_2H_5$)—), 6.53 (2H, s, 2× $H_2$C=C($COOC_2H_5$)—).

Example 8

Synthesis of 2-(tosylmethyl)acrylonitrile (8)

Tosyl iodide (4.88 g, 17 mmol) and methacrylonitrile (1.16 g, 17 mmol) were dissolved in 100 ml carbon tetrachloride and stirred at room temperature for 4 h. The solvent and any iodine formed were then evaporated under vacuum. After the renewed addition of 100 ml carbon tetrachloride, the solution had 4 equivalents of triethylamine added to it and was heated under reflux for 12 h. The resulting brown solution was washed with 5% sodium dithionite solution (2×20 ml), 1N HCl (1× 20 ml) and saturated NaCl solution (1× 20 ml) to remove any remaining iodine and triethylamine. The collected organic phases were dried over 15 g $Na_2SO_4$ and the solvent drawn off on a rotary evaporator. The crude product was purified using column chromatography with pure dichloromethane as mobile solvent. The yield was 789 mg (21% theoretical) 2-(tosylmethyl)acrylonitrile 8 as fine white needles.

$^1$H-NMR (200 MHz, CDCl3) δ=7.73 (d, 8.45 Hz, 2H; Ar—H), 7.33 (d, J=8.45 Hz, 2H; Ar—H), 6.15 (s, 1H; C=H2), 5.94 (s, 1H; C=H2), 3.84 (s, 2H; —SO2-CH2-), 2.41 (s, 3H; Ar—CH3) ppm.

Example 9

Synthesis of 1-methyl-4-((2-phenylallyl)sulfonyl)benzene (9)

Methylstyrene (2.95 g, 25 mmol), tosyl chloride (4.77 g, 25 mmol), Cu(I)Cl (2.48 g, 25 mmol) and triethylamine (2.53 g, 25 mmol) were placed in 70 ml dry acetonitrile and heated under reflux for 3 h under an argon atmosphere. After drawing off the solvent on a rotary evaporator, the crude product was taken up in 30 ml dichloromethane and washed with 1N HCl (2× 20 ml), saturated $NaHCO_3$ solution (1× 20 ml) and saturated NaCl solution (1× 20 ml). After purification using column chromatography with dichloromethane as mobile solvent, 1-methyl-4-((2-phenylallyl)sulfonyl)benzene 9 was obtained in a yield of 3.60 g (53% theoretical).

$^1$H-NMR (200 MHz, $CDCl_3$) δ=7.59 (d, J=7.64 Hz, 2H; Ar—H), 7.5-6.9 (m, 7H; Ar—H), 5.51 (s, 1H; C=$H_2$) 5.14 (s, 1H; C=$H_2$), 4.18 (s, 2H; —$SO_2$—$CH_2$—) 2.32 (s, 3H; Ar—$CH_3$) ppm.

Example 10

Synthesis of 2-(tosylmethyl)acrylic Acid (10)

Bromomethacrylic acid (8.25 g, 50 mmol) was dissolved in 250 ml hot MeOH and NaOH (2 g, 50 mmol) was added to it. Then sodium p-toluene sulfinate (8.91 g, 50 mmol) was added in portions and heated for 2 h under reflux. After drawing off the solvent on a rotary evaporator, the solid residue was taken up in 500 ml water and 2-(tosylmethyl) acrylic acid 10 was precipitated using 1 N HCl. Yield 7.44 g (62% theoretical).

$^1$H-NMR (200 MHz, CDCl$_3$) δ=8.81 (bs, 1H), 7.67 (d, J=8.6 Hz, 2H; Ar—H), 7.27 (d, J=8.6 Hz, 2H; Ar—H), 6.55 (s, 1H; C=H$_2$), 5.94 (s, 1H; C=H$_2$), 4.04 (s, 2H; —SO$_2$—CH$_2$—), 2.36 (s, 3H; Ar—CH$_3$) ppm.

Example 11

Synthesis of N-methyl-N-propyl-2-(tosylmethyl)acrylamide (11)

2-(Tosylmethyl)acrylic acid 10 (3.00 g, 12.5 mmol) was heated under reflux in 30 ml thionyl chloride for 2 h. After drawing off the excess SOCl$_2$, the acid chloride was taken up in 100 ml dichloromethane and 6 equivalents of propyl methyl amine were slowly added to it at 0° C. After stirring at RT for 12 h, the solvent was drawn off on a rotary evaporator and, after being taken up in 20 ml dichloromethane, the crude product was washed with 1 N HCl (2×20 ml) and saturated NaCl solution (1× 20 ml). After purification using column chromatography (PE:EE (1:1)+0.5% acetic acid), 701 mg (19% theoretical) N-methyl-N-propyl-2-(tosylmethyl)acrylamide 11 was obtained.

$^1$H-NMR (200 MHz, CDCl$_3$) δ=7.78 (d, J=8.1 Hz, 2H; Ar—H), 7.34 (d, J=8.1 Hz, 2H; Ar—H), 5.51 (bs, 1H; C=H$_2$), 5.41 (s, 1H; C=H$_2$), 4.09 (s, 2H; —SO$_2$—CH$_2$—), 3.5-2.7 (m, 5H; N—C$\underline{H}_3$, N—C$\underline{H}_2$—CH$_2$—CH$_3$), 2.38 (s, 3H; Ar—CH$_3$), 1.7-1.3 (m, 2H; N—CH$_2$—C$\underline{H}_2$—CH$_3$), 0.85 (t, J=7.5 Hz, 3H; N—CH$_2$—CH$_2$—C$\underline{H}_3$) ppm.

Example 12

Synthesis of 14-methyl-13-oxo-3,6,9,12-tetraoxa-pentadec-14-en-1-yl 2-(tosylmethyl)acrylate (12)

precipitated out). The crude product was purified using column chromatography with a mixture of PE/EE 1/3. (R$_f$~0.38). Yield 24%.

$^1$H-NMR (200 MHz, CDCl$_3$, δ): 7.70 (d, J=8.2 Hz, 2H; Ar—H), 7.31 (d, J=8.2 Hz, 2H; Ar—H), 6.49 (s, 1H; =CH$_2$), 6.10 (m, 1H; =CH$_2$), 5.86 (s, 1H; =CH$_2$), 5.50 (m, 1H; =CH$_2$), 4.27 (m, 2H; —OOC—CH$_2$—), 4.12 (m, 4H; —OOC—CH$_2$—, —SO$_2$—CH$_2$—), 3.71 (m, 2H; OOC—CH$_2$—C$\underline{H}_2$—), 3.63 (m, 10H; —CH$_2$—O—CH$_2$—CH$_2$—O—CH$_2$—CH$_2$—), 2.41 (s, 6H; Ar—CH$_3$) 1.92 (m, 3H; —CO—C—CH$_3$).

$^{13}$C-NMR (50 MHz, CDCl$_3$, δ): 164.9 (C=O), 145.0 (C4), 136.2 (C4) 135.5 (C4), 133.7 (C2), 129.8 (C3), 129.0 (C4), 128.9 (C3), 125.9 (C2), 70.7 (C2), 69.2 (C2), 68.9 (C2), 64.6 (C2), 64.0 (C2), 57.7 (C2), 21.8 (C1), 18.4 (C1).

Example 13

Synthesis of 2-(methylsulfonylmethyl)-acrylic Acid Ethyl Ester (13)

Ethyl 2-bromomethylacrylate (1.1 g, 5.8 mmol), sodium methanesulfinate (0.7 g, 6.7 mmol) and 0.1 g polyethylene oxide 400 were placed in 10 ml absolute THF under an argon atmosphere. Heating then took place under reflux for 20 hours, wherein the progress of the reaction was monitored using NMR and TLC. Once the reaction was complete, the reaction solution was diluted with 10 ml deionized water and 10 ml diethyl ether. The aqueous phase was extracted three times with 25 ml diethyl ether in each case. The combined organic phases were then washed with saturated saline solution, dried over sodium sulfate and evaporated on a rotary evaporator. The crude product obtained was purified using column chromatography with a mixture of PE/EE 1/1. (R$_f$~0.45). Yield 33%.

Tetraethylene glycol dimethacrylate (TTEGDMA, 14.6 g, 44.7 mmol) and 4-toluenesulfonyl iodide (12.6 g, 44.7 mmol) were stirred together in CH$_2$Cl$_2$ (approx. 100 ml) at room temperature under yellow light. The synthesis took place analogously to the synthesis of Example 2. Triethylamine (22.6 g, 223.4 mmol) was added dropwise (solid $^1$H-NMR (200 MHz, CDCl$_3$, δ): 6.64 (s, 1H; =CH$_2$), 6.15 (s, 1H; =CH$_2$), 4.28 (q, J=7.1 Hz, 2H; —COO—C$\underline{H}_2$—CH$_3$), 4.06 (s, 2H; —SO$_2$—C$\underline{H}_2$—C—), 2.90 (s, 3H; —SO$_2$—CH$_3$), 1.33 (t, J=7.1 Hz, 3H; —COO—CH$_2$—C$\underline{H}_3$).

$^{13}$C-NMR (50 MHz, CDCl$_3$, δ): 165.3 (C=O), 133.9 (C2), 129.1 (C4), 61.9 (C2), 56.4 (C2), 40.5 (C1), 14.1 (C1).

Example 14

Synthesis of 2-methylene-3-[(4-methylphenyl)sulfonyl]butyric Acid Methyl Ester (14)

(Z)-Methyl-2-(bromomethyl)but-2-enoate (2.7 g, 14.0 mmol) and 0.5 g polyethylene oxide 400 were placed in 15 ml absolute THF and cooled to −20° C. Sodium p-toluenesulfinate (0.8 g, 4.7 mmol) was then added slowly. Stirring was carried out at −20° C. for 10 hours. Purification was carried out using column chromatography with a mixture of PE/EE 2/1. ($R_f$~0.50). Yield 36%.

$^1$H-NMR (200 MHz, CDCl$_3$, δ): 7.69 (d, J=8.2 Hz, 2H; Ar—H), 7.30 (d, J=8.2 Hz, 2H; Ar—H), 6.53 (s, 1H; =CH$_2$), 5.98 (s, 1H; =CH$_2$), 4.58 (q, J=7.2 Hz, 1H; —SO$_2$—CH—), 3.60 (s, 3H; —COO—CH$_3$), 2.42 (s, 3H; Ar—CH$_3$), 1.54 (d, J=7.2 Hz, 3H; —SO$_2$—CH—C$\underline{H}_3$).

Example 15

Synthesis of the Thermolabile Dimethacrylate 3-oxo-2-(2,2,4-trimethyl-6-{2-[2-(methacryloyloxy)-ethoxycarbonyl]-3-oxo-butyrylamino}-hexylcarbamoyl)-butyric Acid 2-(methacryloyloxy)-ethyl Ester 15

Sodium (0.50 g; 2.2 mmol) in diethyl ether (400 ml) was placed in an apparatus heated under argon and (2-acetoacetoxy)ethyl methacrylate (85.69 g; 0.40 mol) was added dropwise. The reaction mixture was stirred for 20 h at RT and then cooled in an ice bath to 0° C. 2,2,4-Trimethyl-1,6-diisocyanatohexane (42.06 g; (0.20 mol) was slowly added dropwise. The reaction mixture was stirred, after the end of the addition, for a further 2 h accompanied by ice cooling and then at ambient temperature. After 48 h the suspension was filtered and the filtrate was washed with hydrochloric acid (1N; 2×100 ml), water (100 ml) and saturated aqueous NaCl solution (100 ml), dried over Na$_2$SO$_4$, filtered and concentrated on a rotary evaporator. The yellowish oil was dissolved in dichloromethane (100 ml) and filtered via a frit filled with silica gel (silica gel 60, n-hexane/ethyl acetate 1:1). The filtrate was concentrated on a rotary evaporator and the residue was dried under a fine vacuum. The dimethacrylate 15 (105.42 g, 83% yield) was obtained as a yellowish oil.

$^1$H-NMR (CDCl$_3$, 400 MHz): δ=0.95 (s, 6H), 0.98-1.02 (m, 3H), 1.09-1.68 (m, 5H), 1.95 (s, 6H), 2.41-2.43 (m, 6H), 3.05-3.36 (m, 4H), 4.44 (s, 8H), 5.61 (s, 2H), 6.13 (s, 2H), 9.10-9.30 (m, 2H), 18.70-18.73 (m, 2H).

Example 16

Preparation of Composites with Transfer Reagent 1 from Example 1

Figure 1:
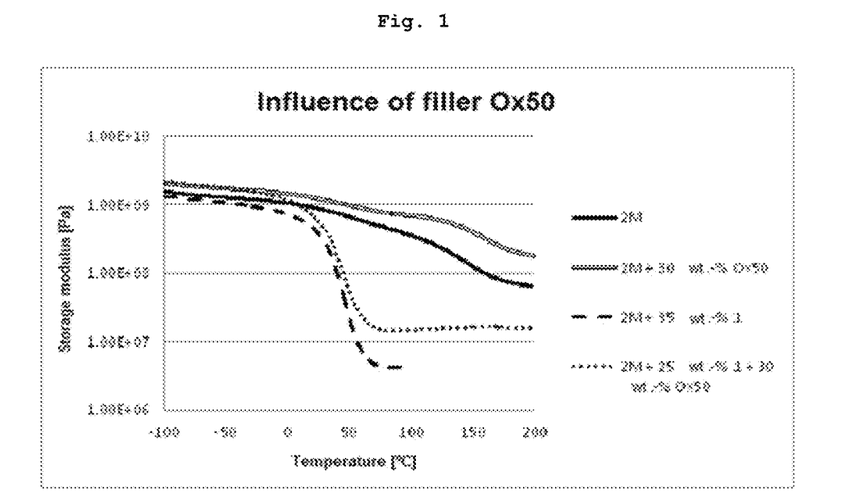
FIG. 1 shows a storage modulus graph for cured resin samples and composites.

A 1/1 mixture (mol/mol) of the monomers UDMA and D$_3$MA was prepared (resin mixture 2M). Part of this mixture was mixed with monomer 1 from Example 1. The second mixture had the following composition: UDMA (39 wt.-%), D$_3$MA (26 wt.-%) and 1 (35 wt.-%). The photoinitiator Ivocerin® (1 wt.-%) was added to both mixtures. Composite pastes based on these mixtures were prepared by adding 30 wt.-% of the pyrogenic silicic acid Ox50. The composite paste with monomer 1 had the total composition: UDMA (27 wt.-%), D$_3$MA (18 wt.-%), 1 (24.3 wt.-%), initiator (0.7 wt.-%) and Ox50 (30 wt.-%). The formulations were poured into silicone moulds and polymerized in a Lumamat 100 (Ivoclar AG) using program 2 (P2: 10 min irradiation with an intensity of approx. 20 mW/cm$^2$). The rods were turned and cured again using P2. The test rods were ground and then measured on an Anton Paar Rheometer MCR301 with a CTD oven (Convection Temperature Control) and an installed solid clamping device (SRF12 for rectangular cross-sections up to 12 mm). The heating rate set was 2° C./min. All samples were heated from −100° C. to 200° C. and oscillated at a constant frequency of 1 Hz and 0.1% deflection. The storage modulus graphs represented in FIG. 1 show that the addition of transfer reagent 1 both in the case of the cured resin sample and in the case of the composite similarly leads to a reduction in the glass transition temperature and to a deeper and significantly narrower glass transition range.

TABLE 1

Glass transition temperatures

| Formulation | $T_G$ [° C.] |
|---|---|
| 2M$^{a)}$* | 148 |
| 2M + Ox50* | 162 |
| 2M + monomer 1 | 50 |
| 2M + monomer 1 + Ox50 | 50 |

$^{a)}$2M: UDMA/D$_3$MA (1/1)
*Comparison example

Example 17

Preparation of Composites with Transfer Reagent 2 Example 2

Figure 2:
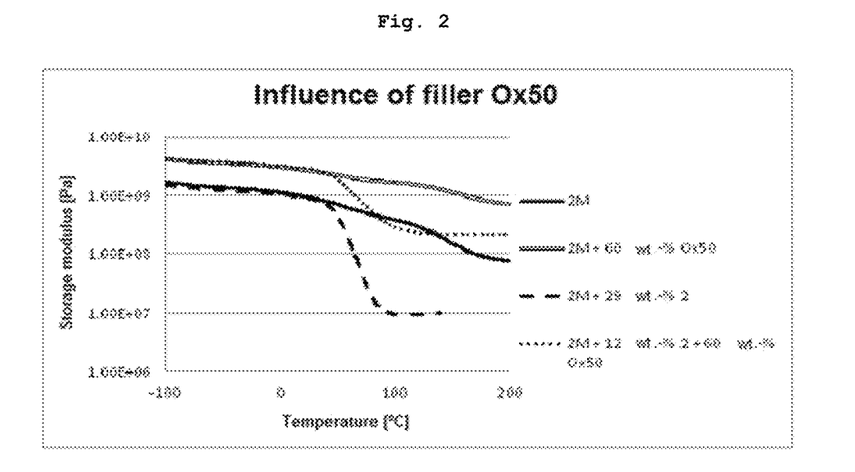
FIG. 2 shows a storage modulus graph for cured resin samples and composites of different compositions than shown in FIG. 1.

Test pieces were prepared and investigated analogously to Example 4. The following formulations were used: 1/1 mixture (mol/mol) of UDMA and D$_3$MA (mixture 2M) and a mixture of UDMA (43 wt.-%), D$_3$MA (28 wt.-%) with monomer 2 (29 wt.-%). Corresponding composite pastes were obtained by adding 60 wt.-% Ox50. The composite paste with monomer 2 had the following total composition: UDMA (17 wt.-%), D$_3$MA (11 wt.-%), 2 (12 wt.-%) and Ox50 (60 wt.-%). FIG. 2 again shows the storage modulus as a function of the temperature for the unfilled and filled resins. The storage modulus graphs shown in FIG. 2 show that the addition of transfer reagent 2 (Example 2) both in the case of the unfilled resin and in the case of the composite leads to a significantly narrower glass transition range with a reduced glass transition temperature (T$_G$).

TABLE 2

Glass transition temperatures

| Formulation | T$_g$ [° C.] |
|---|---|
| 2M$^{a)}$* | 148 |
| 2M + Ox50* | 157 |
| 2M + monomer 2 | 73 |
| 2M + monomer 2 + Ox50 | 78 |

$^{a)}$2M: UDMA/D$_3$MA (1/1)
*Comparison example

Example 18

Determination of the Debonding-on-Demand Properties

A two-component, light-curing and dual-curing fixing cement Variolink II (Ivoclar Vivadent AG, the cement is based on a monomer mixture of bis-GMA, UDMA and TEGDMA, and barium glass, Ba—Al-fluorosilicate glass, SiO$_2$—ZrO$_2$ mixed oxide and ytterbium trifluoride are contained as fillers) was modified using monomer 3 from Example 3 for crown removal experiments. For this, 9.066 g of the component Variolink II base transparent was mixed with 0.934 g monomer 3 for 2×3 minutes on the highest setting at 0.2 bar residual pressure (planetary mixer DAC 600.2 VAC-P, Hauschild & Co. KG, Hamm, Germany). In the same way, 9.017 g of the component Variolink II catalyst transparent/thin was modified with 0.983 g monomer 3.

The investigation of the crown removal forces was carried out both with the modified material Variolink II (see above) and with unmodified Variolink II. For this, test crowns were fixed to matching stumps made of zirconium dioxide (truncated cone geometry: cone angle 40°, height 3.3 mm, curved surface area 56.3 mm$^2$, predetermined cement gap 50 μm). The bonding surfaces of the test system were each freshly sandblasted beforehand (Al$_2$O$_3$ 110 μm, 1 bar) and surface-conditioned with the adhesion promoter Monobond Plus (Ivoclar Vivadent AG, residence time 60 s). For the fixing, in each case 250 mg base paste and catalyst paste (test groups 1 and 2: Variolink II base transparent, Variolink II catalyst transparent/thin; test groups 3 and 4: Variolink II base transparent modified according to the above example, Variolink II catalyst transparent/thin modified according to the above example) were mixed by hand on a mixing block using a spatula for 10 s and approximately half of the mixture was poured into the crown. The crown was then set on the stump and loaded with a static weight of 2 kg. Immediately afterwards, the excess was removed using a Microbrush (Microbrush, Grafton, USA) and then, approx. 30 s after the start of the loading, it was exposed to light from 2 sides for 40 s in each case using a light-polymerization device (Bluephase G2, Ivoclar Vivadent AG; High Power). The load was then removed from the test body and the latter was stored for at least 16 h at 37° C. in a drying oven until measurement.

To determine the crown removal forces, the test bodies from test groups 1 and 3 were measured in a water bath temperature controlled to 23° C. and the test bodies from groups 2 and 4 were measured in a water bath temperature controlled to 60° C. (temperature-controlled container for medical experiments, Zwick-Roll GmbH & Co. KG, Ulm, Germany) using a materials testing machine (2010, Zwick-Röll). Before the start of the measurement, the crowns were each temperature-controlled for at least 2 min. in the corresponding water bath. The crowns were then removed in a position-controlled manner at a traverse speed of 1 mm/min., wherein the highest force arising was recorded as the crown removal force. The results in Table 3 demonstrate a significantly reduced crown removal force at 60° C. for the cement with compound 3 according to the invention.

TABLE 3

Crown removal forces

| Test group 1* | Test group 2* | Test group 3 | Test group 4 |
|---|---|---|---|
| 1101 N +/− 320 N | 808 N +/− 168 N | 1259 N +/− 238 N | 558 N +/− 264 N |

*Comparison example

Example 19

Preparation and Characterization of Polymers with Dimethacrylates and Transfer Reagents A 1/1 mixture (mol/mol) of UDMA and D$_3$MA (2M) as well as mixtures of UDMA, D$_3$MA and in each case one transfer reagent (compounds nos. 1, 2, 5-14) was prepared according to Table 3. The formulations additionally contained 1 wt.-% Ge initiator (Ivocerin). To check the photo-reactivity, the formulations prepared were measured using a photorheometer (MCR 302 WESP model, Anton Paar). A plate-plate measuring system of the PP25 type was used and the measuring gap was set to 0.1 mm. Before and during curing with a UV lamp (Omnicure 2000 model; 400-500 nm; 1 W/cm$^2$ and 3 W/cm$^2$ respectively), the storage modulus and loss modulus of the sample were measured in the oscillation mode (1% deflection, 1 Hz).

The double-bond conversion (DBC) achieved at the gel point (intersection of the storage modulus and the loss modulus) serves as a measure of the polymerization shrinkage occurring. The double-bond conversion up to the gel point does not lead to the build-up of stresses as the polymerization shrinkage occurring is compensated for by flow processes. The higher the double-bond conversion is at the gel point, the lower are consequently the double-bond conversion and the polymerization shrinkage in the gel condition, which thus also leads to a lower polymerization shrinkage force. To determine the glass transition, the formulations were poured into silicone moulds and polymerized in a light furnace (Lumamat 100 model, Ivoclar AG) using program 2 (P2: 10 min irradiation with an intensity of approx. 20 mW/cm$^2$). The rods were turned and cured again using P2. The test rods were ground and then measured on a rheometer (MCR 302 model) with a CTD oven (Convection Temperature Control) and an installed solid-clamping device (SRF12 for rectangular cross-sections up to 12 mm). The heating rate set was 2° C./min. All samples were heated from −100° C. to 200° C. and oscillated at a constant frequency of 1 Hz and 0.1% deflection.

The glass transition temperatures shown in Table 4 (maxima of the loss modulus graphs) show that the addition of the transfer reagents leads to a deeper and significantly narrower glass transition range, which makes debonding-on-demand substantially easier in the compositions according to the invention. Moreover, it can be seen that the double-bond conversion at the gel point is increased by the transfer reagents. A lower shrinkage stress is therefore to be expected because stresses can be dissipated by flow processes up to the gel point.

TABLE 4

| Formulation | $T_G$ [° C.] | HW [° C.] | DBC [%] |
|---|---|---|---|
| 2M[a]* | 150 | 152 | 18 |
| 2M[c]* | 148 | 145 | 18 |
| 2M + 35 wt.-% 1 | 50 | 28 | [b] |
| 2M + 29 wt.-% 2 | 75 | 32 | 23 |
| 2M + 29 wt.-% 5 | 48 | 51 | 30 |
| 2M + 14 wt.-% 6 | 134 | 51 | 24 |
| 2M + 16 wt.-% 7 | 68 | 51 | 29 |
| 2M + 6 wt.-% 8[c] | 129 | 93 | 51 |
| 2M + 7 wt.-% 9[c] | 126 | 82 | 28 |
| 2M + 6 wt.-% 10[c] | 114 | 55 | 25 |
| 2M + 34 wt.-% 11[c] | 74 | 57 | 36 |
| 2M + 45 wt.-% 12 | 64 | 23 | [b] |
| 2M + 20 wt.-% 13 | 66 | 26 | [b] |
| 2M + 26 wt.-% 14 | 65 | 74 | [b] |

*Comparison example
$T_G$ Glass transition temperature
HW Half width
DBC Double-bond conversion at the gel point
[a]2M: UDMA/D$_3$MA (1/1)
[b] Not measured
[c]Curing with 3 W/cm$^2$ Example 20

Determination of the Efficiency of the Combination of β-allylsulfones with the Thermolabile Dimethacrylate 15

The following polymer rods were prepared in analogy to Example 16 in order to test the efficiency of the combination of chain regulating β-allylsulfones with the thermolabile dimethacrylate 15 (=capped isocyanate monomer of Example 15):
A1* D$_3$MA and 2 (chain transfer agent from Example 2, 25 DB, 41 wt.-%),
A2* equimolar dimethacrylate formulation of D$_3$MA and 15 (thermolabile dimethacrylate from Example 15; 67 wt.-%),
A3 A2 and 1 (chain transfer agent from Example 1; 25 DB, 36 wt.-%),
A4 A2 and 2 (chain transfer agent from Example 2, 25 DB, 31 wt.-%),
A5 equimolar formulation of 15 (thermolabile dimethacrylate from Example 15) and 2 (chain transfer agent from Example 2, 50 DB, 50 wt.-%)

Comparison Example

Figure 3:
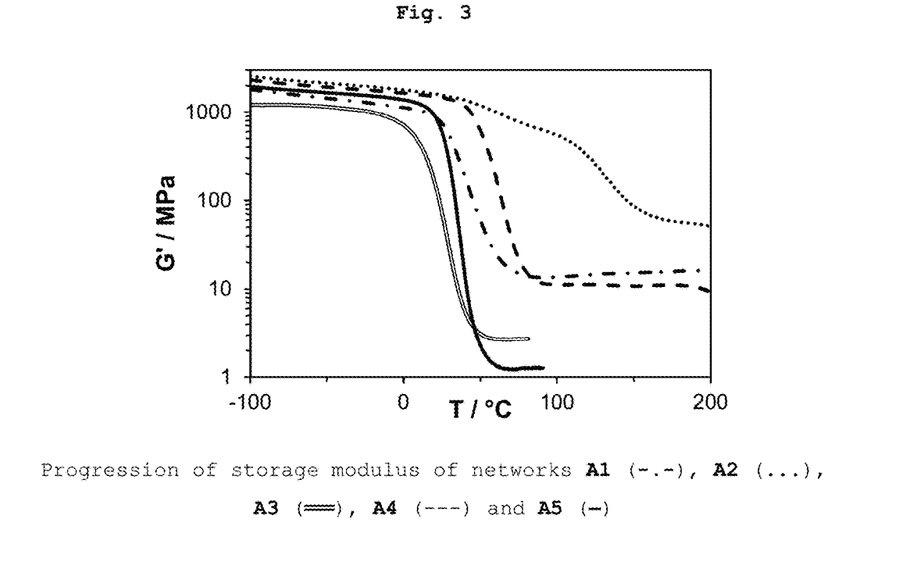
FIG. 3 shows Dynamic Mechanical Thermal Analysis (DMTA) results for five samples.
Figure 4:
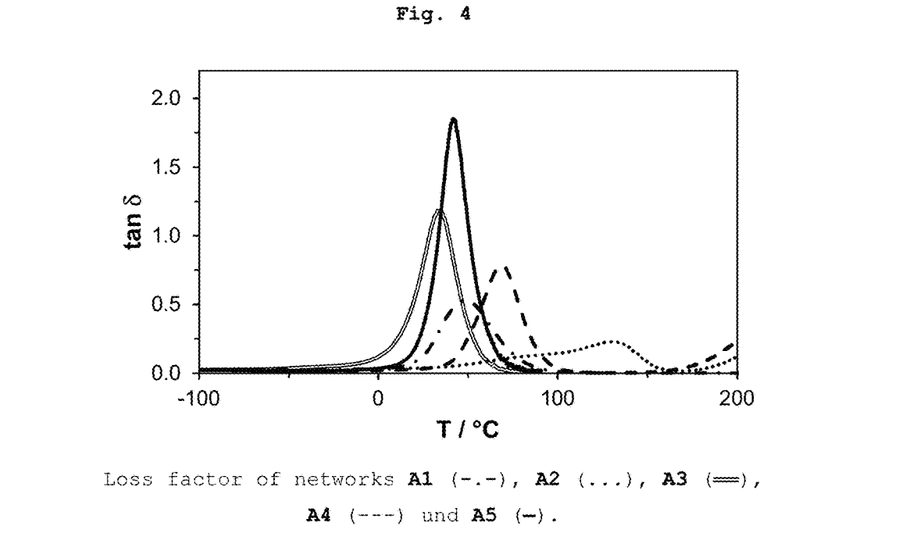
FIG. 4 shows DMTA results for five samples.

DMTA experiments were carried out in order to test whether an induced gas formation by a capped isocyanate, for destroying the network, is permitted by the control of the network (less dens network). The five samples described above were oscillated according to Example 16 on an Anton Paar Rheometer (MCR 301) equipped with a DMTA unit over a temperature range from −100 to 200° C. at a deflection of 0.1% and a frequency of 1 Hz. The results obtained are shown in FIGS. 3 and 4 and in Table 5.

Comparison example A1 represents a modified network with sharp glass transition. Here no thermolabile cross linking agent is included.

Network A2 (a pure dimethacrylate network of D$_3$MA and the thermolabile dimethacrylate cross linking agent 15, 67 wt.-%) was also used as a comparison and shows no sharp thermal transition over the whole temperature range. The formation of gas induced by decomposition of the thermolabile dimethacrylate cross linking agent 15 could not be observed due to the dense network.

By adding the β-allylsulfones 1 or 2 according to the invention (25 DB; A3 with 36 wt.-% or A4 with 31 wt.-%) a debonding-on-demand range could be set in a targeted temperature interval. In addition, the cross linking density of A3 and A4 was reduced with regard to A2 by control of the radical photopolymerization. Network A5 (50 DB, 50 Gew.-%) represents a more homogenous network (FWHM=18° C.) with even lower cross linking density (G'$_r$<2 Mpa). It can easily be seen that due to the high content of the β-allylsulfones according to the invention thermal glass transition already starts at room temperature and that the material is relatively soft. Nevertheless, mechanical properties can be improved by the addition of monomers such as Bis-GMA.

TABLE 5

DMTA results for samples A1-6

| Sample | Composition | G'$_{20}$/ MPa | $T_g$/ ° C. | fwhm/ ° C. | G'$_r$/ MPa |
|---|---|---|---|---|---|
| A1* | D3MA/2 (41 wt.-%) | 882 | 49 | 34 | 13.5 |
| A2* | D3MA/15 (67 wt.-%) | 1610 | 131 | 71 | 50.8 |
| A3 | A2/1 (36 wt.-%) | 160 | 34 | 24 | 2.7 |
| A4 | A2/2 (31 wt.-%) | 1510 | 69 | 26 | 9.3 |
| A5 | 15/2 (50 wt.-%) | 920 | 42 | 18 | 1.3 |

*Comparative example

Table 5 shows the characteristic values of the performed DMTA analysis and describes that by using the β-allylsulfones 1 and 2 according to the invention the network density of the photopolymers can be adjusted and that thereby a sharp thermal glass transition is obtained (FWHM=18-26° C.). This is a positive effect, which can be used for a debonding-on-demand. This is even more visible on the basis of the very narrow glass transition for A5 (with 50 wt.-% 2, FWHM=18° C.), wherein the Tg of 42° C. is here already very low. Turning now to the polymer rods of examined networks A1-A5 after the DMTA measurement (FIG. 5), it can be seen that the capped isocyanate 15 does not decompose due to the high cross linking density of the network A2 and there is no appreciable gas formation. In the much looser networks A3 and A4 (36 or 31 wt.-% 2) a discoloration can already be seen, which points to a thermally induced reaction. Nevertheless, the storage modulus of networks A2-A4 remains unchanged and the networks are not destroyed by the heat treatment.

Figure 5:
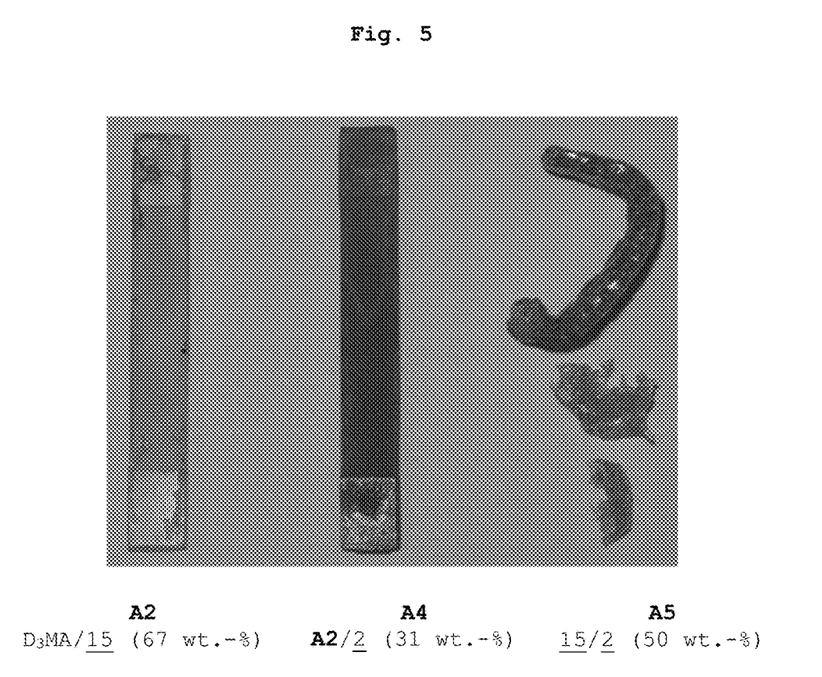
FIG. 5 shows a polymers rods of examined networks after DMTA measurements. storage modulus graph for cured resin samples and composites of different compositions than shown in FIG. 1.

If, however, network A5 in FIG. 5 (right) is considered, one can see that here an induced gas formation occurred during the heat treatment, caused by 15. The gas formation could easily be observed visually beyond about 110° C. The polymer network is inflated by the gas bubbles and the resulting porosity causes a deterioration of mechanical properties. By this it could be shown that dependent on the network density an induced cleavage of the thermolabile dimethacrylate cross linking agent 15 and a subsequent gas formation occurs. This effect can be used for targeted debonding-on-demand.

The invention claimed is:

1. Radically polymerizable dental material which contains at least one compound of Formula I:

with:
A=H; —CN; a phenyl residue which can carry one or more substituents; or an aliphatic linear or branched $C_1$-$C_{20}$ alkylene residue which can be interrupted by one or more 1,4-phenylene groups, urethane groups, O or S and which can carry in the terminal position a polymerizable vinyl, (meth)acryloyloxy or (meth)acrylamide group;

$R^1$=H, an aliphatic linear or branched $C_1$-$C_9$ alkyl radical, tolyl or phenyl;

L=$SO_2R^3$, wherein $R^3$ is $CH_3$ or tolyl;

X=—COO—, —CON($R^{10}$)— or is absent, wherein the bond to A takes place via O or N and $R^{10}$=H; or is an aliphatic linear or branched $C_1$-$C_{20}$ alkylene residue which can be interrupted by one or more O or S and which can carry in the terminal position a polymerizable vinyl, (meth)acryloyloxy, (meth)acrylamide group, —C(=$CH_2$)—$COOR^{11}$ or —C(=$CH_2$)—CO—$NR^{12}R^{13}$, wherein $R^{11\text{-}13}$ in each case independently of each other are a linear or branched $C_{1\text{-}6}$ residue;

n=an integer from 1 to 6, and at least one thermolabile radically polymerizable compound and/or at least one photolabile radically polymerizable compound.

2. Dental material according to claim 1, wherein the variables of Formula I have the following meanings:

A H, —CN, a phenyl residue, an aliphatic linear or branched $C_1$-$C_{15}$ alkyl residue which can be interrupted by one or more 1,4-phenylene groups, urethane groups or O and which can carry in the terminal position a polymerizable (meth)acryloyloxy group;

$R^1$ H, phenyl, tolyl, an aliphatic linear $C_1$-$C_3$ alkyl radical;

L $SR^2$ or $SO_2R^3$, wherein $R^{2\text{-}3}$ in each case independently of each other are an aliphatic linear or branched $C_1$-$C_{20}$ alkylene residue which can be interrupted by O and which can carry in the terminal position a polymerizable (meth)acryloyloxy group or —C(=$CH_2$)—$COOR^{11}$, wherein $R^{11}$ is a linear or branched $C_{1\text{-}3}$ radical; or a phenyl residue which can carry one or more substituents;

X —COO— or —CON($R^{10}$)—, wherein $R^{10}$ is methyl, or is absent;

n 1 or 2.

3. Dental material according to claim 2, wherein the variables of Formula I have the following meanings:

A a saturated, linear aliphatic hydrocarbon residue with 1 to 12 carbon atoms which can be interrupted by one or more 1,4-phenylene groups, urethane groups or O and which can carry a methacryloyloxy group, X —COO— or —CON($R^{10}$)—, wherein $R^{10}$ is methyl, or is absent;

$R^1$ H,
n 1 or 2.

4. Dental material according to claim 3, wherein the variables of Formula I have the following meanings:

A a saturated, linear aliphatic hydrocarbon residue with 6 to 12 carbon atoms which can be interrupted by 1 to 3 O atoms,

X —COO—;

$R^1$ H,

L $SO_2R^3$, wherein $R^3$ is $CH_3$ or tolyl, n 1 or 2.

5. Dental material according to claim 1, which contains, as thermolabile radically polymerizable compound, a thermolabile multifunctional (meth)acrylate or (meth)acrylamide and/or, as photolabile radically polymerizable compound, at least one photolabile multifunctional (meth)acrylate or (meth)acrylamide.

6. Dental material according to claim 1, which contains, as the thermolabile radically polymerizable compound, a monomer which is selected from polyfunctional (meth)acrylates or (meth)acrylamides with at least one thermolabile group between two (meth)acryl or (meth)acrylamide groups, the Diels-Alder adduct from furfuryl methacrylate and N-(3-(methacryloyloxy)propyl)-maleimide, the reaction products of N-hydroxy-(meth)acrylamide with di- or triisocyanates, hexamethylene-1,6-diisocyanate (HDI), 2,2,4-trimethylhexamethylene-1,6-diisocyanate or the HDI trimer, products which can be obtained by the stoichiometric reaction of di- or triisocyanates with 1-hydroxymethylacrylic acid esters, 1-hydroxymethylacrylic acid ethyl ester, with β-keto ester (meth)acrylates or 2-acetoacetoxyethyl methacrylate, thermolabile cross-linking monomers which release gas, the esterification products of azobis(4-cyanovaleric acid) with hydroxyalkyl (meth)acrylates, hydroxyethyl (meth)acrylate, hydroxylpropyl (meth)acrylate, N-(hydroxyalkyl)(meth)acrylamides, N-(5-hydroxypentyl)methacrylamide or N-methyl-N-(2-hydroxyethyl)acrylamide.

7. Dental material according to claim 1, which contains, as the photolabile radically polymerizable compound, a monomer with a photolabile group which is selected from benzoin ethers, oxyalkylphenylacetophenones, dialkyloxyacetophenones, benzoyl diphenylphosphine oxides, dibenzoyl phenylphosphine oxides, dialkyl benzoyl and dialkyl dibenzoyl germanium derivatives.

8. Dental material according to claim 1, which contains, as the photolabile radically polymerizable compound, a monomer with one photolabile group and two polymerizable (meth)acrylate groups, bis-(4-methacryloyloxybenzoyldi-ethyl germanium, bis-{4-[2-(methacryloyloxy) diethylcarbamoyloxybenzoyl}diethyl germanium, bis-[3-(methacryloyloxymethyl)-2,4,6-trimethylbenzoyl]-phenylphosphine oxide or methacrylic acid 2-[2-(4-{2-methyl-2-[2-(methacryloyloxy)ethylcarbamoyloxy]-propionyl}-phenoxy)-ethoxycarbonylamino]ethyl ester.

9. Dental material according to claim 1, which additionally contains at least one multifunctional (meth)acrylate or a mixture of mono- and multifunctional (meth)acrylates.

10. Dental material according to claim 1, which additionally contains at least one radically polymerizable, acid-group-containing monomer.

11. Dental material according to claim 1, which additionally contains at least one initiator for the radical polymerization.

12. Dental material according to claim 1, which additionally contains an initiator(s), wherein the dental material comprises 0.5 to 60 wt.-% of at least one compound of general formula I,
0.01 to 5.0 wt.-% initiator(s) for the radical polymerization, and
1 to 60 wt.-% difunctional thermo- and/or photolabile (meth)acrylate(s), in each case relative to the total mass of the dental material.

13. Dental material according to claim 12, which may additionally contain a monofunctional (meth)acrylate(s), a filler(s), an expanding additive(s), a radiation-to-heat converter(s), a solvent(s) and other additive(s), and further contains a multifunctional (meth)acrylate(s), and has the following composition:
   (a) 1 to 80 wt.-% multifunctional (meth)acrylate(s),
   (b) 0.01 to 5.0 wt.-% wt.-% initiator(s),
   (c) 0.5 to 60 wt.-% of at least one compound of general formula I,
   (d) 0 to 50 wt. % monofunctional (meth)acrylate(s),
   (e) 1 to 60 wt.-% difunctional thermo- and/or photolabile (meth)acrylate(s),
   (f) 0 to 80 wt.-% filler(s),
   (g) 0 to 40 wt.-% expanding additive(s) and/or radiation-to-heat converters,
   (h) 0 to 60 wt.-% solvent(s) and
   (i) 0 to 5 wt.-% other additive(s),
   in each case relative to the total mass of the dental material.

14. Dental material according to claim 11, wherein the initiator comprises a photoinitiator.

15. Dental material according to claim 12, which contains 1.0 to 50 wt.-% of at least one compound of general formula I,
   0.1 to 5.0 wt.-% initiator(s) for the radical polymerization, and
   5 to 50 wt.-% difunctional thermo- and/or photolabile (meth)acrylate(s), in each case relative to the total mass of the dental material.

16. Dental material according to claim 12, which contains 1.0 to 40 wt.-% of at least one compound of general formula I
   0.1 to 3.0 wt.-% initiator(s) for the radical polymerization, and
   5 to 40 wt.-% difunctional thermo- and/or photolabile (meth)acrylate(s), in each case relative to the total mass of the dental material.

17. Dental material according to claim 13, which has the following composition:
   (a) 10 to 70 wt.-% multifunctional (meth)acrylate(s),
   (b) 0.1 to 5.0 wt.-% initiator(s),
   (c) 1.0 to 50 wt.-% of at least one compound of general formula I,
   (d) 0 to 40 wt.-% monofunctional (meth)acrylate(s),
   (e) 1 to 60 wt.-% difunctional thermo- and/or photolabile (meth)acrylate(s),
   (f) 0 to 70 wt.-% filler(s),
   (g) 0 to 30 wt.-% expanding additive(s) and/or radiation-to-heat converters,
   (h) 0 to 50 wt.-% solvent(s) and
   (i) 0 to 3 wt.-% other additive(s),
   in each case relative to the total mass of the dental material.

18. Dental material according to claim 13, which has the following composition:
   (a) 10 to 60 wt.-% multifunctional (meth)acrylate(s),
   (b) 0.1 to 3.0 wt.-% initiator(s),
   (c) 1.0 to 40 wt.-% of at least one compound of general formula I,
   (d) 0 to 30 wt.-% monofunctional (meth)acrylate(s),
   (e) 5 to 50 wt.-% difunctional thermo- and/or photolabile (meth)acrylate(s),
   (f) 0 to 70 wt.-% filler(s),
   (g) 5 to 30 wt.-% expanding additive(s) and/or radiation-to-heat converters,
   (h) 1 to 50 wt.-% solvent(s) and
   (i) 0.5 to 3 wt.-% other additive(s),
   in each case relative to the total mass of the dental material.

19. Dental material according to claim 13, which has the following composition:
   (a) 10 to 60 wt.-% multifunctional (meth)acrylate(s),
   (b) 0.1 to 3.0 wt.-% initiator(s),
   (c) 1.0 to 40 wt.-% of at least one compound of general formula I,
   (d) 0 to 30 wt.-% monofunctional (meth)acrylate(s),
   (e) 5 to 40 wt.-% difunctional thermo- and/or photolabile (meth)acrylate(s),
   (f) 0 to 70 wt.-% filler(s),
   (g) 5 to 30 wt.-% expanding additive(s) and/or radiation-to-heat converters,
   (h) 1 to 50 wt.-% solvent(s) and
   (i) 0.5 to 3 wt.-% other additive(s),
   in each case relative to the total mass of the dental material.

20. Dental material according to claim 1, wherein the substituents in A comprise one or more of $CH_3$, $C_2H_5$, OH, $OCH_3$, O—$COCH_3$, a polymerizable vinyl, (meth)acryloyloxy or (meth)acrylamide group.

21. Dental material according to claim 1, wherein the substituents in $R^{2-9}$ comprise one or more of $CH_3$, $C_2H_5$, OH, $OCH_3$, —O—$COCH_3$, a polymerizable vinyl, (meth)acryloyloxy, (meth)acrylamide group, —C(=$CH_2$)—$COOR^{11}$ or —C(=$CH_2$)—CO—$NR^{12}R^{13}$.

22. Dental material according to claim 2, wherein the substituents in $R^{2-3}$ comprise one or more of $CH_3$, $C_2H_5$, $OCH_3$ and/or O—$COCH_3$.

* * * * *